United States Patent [19]

Van den Berg et al.

[11] Plant 4,690

[45] Apr. 14, 1981

[54] IMPATIENS PLANT

[75] Inventors: Cornelis P. Van den Berg; James C. Mikkelsen, both of Ashtabula, Ohio

[73] Assignee: Mikkelsens, Inc., Ashtabula, Ohio

[21] Appl. No.: 103,086

[22] Filed: Dec. 12, 1979

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Red Planet, and particularly characterized by the combined characteristics of good self-branching; spreading habit; highly variegated foliage; striking velvet-like deep-red flowers; early flowering; suitability for growing both outside in full sunlight and in hanging baskets; and by its good keeping quality both outside in full sunlight and in hanging baskets.

1 Drawing Figure

The present invention relates to a new and distinct cultivar of impatiens plant, hereinafter referred to by the cultivar name Red Planet.

Red Planet is the product of a planned breeding program and was originated from a cross made by us in Ashtabula, Ohio. The seed parent was an unnamed cultivar identified by number 76-398-2, and the pollen parent was Satellite, a commercially known but unpatented cultivar. Asexual reproduction of Red Planet by terminal or stem cuttings taken by us in Ashtabula, Ohio has shown that the combination of characteristics as herein disclosed for Red Planet are stable and retained through successive generations of asexual reproduction.

The following characteristics distinguish Red Planet from both its parent varieties and other cultivated impatiens of this type known and used in the floriculture industry:

1. The new cultivar was selected specifically for flower color, earliness of flowering, floriferousness and a spreading habit, which makes the cultivar suitable for growing in a hanging basket.

2. Flowers are velvet-like deep red, appear in an early stage of plant development, and the plant continues to flower abundantly throughout the growing season.

3. Flowers are approximately 50 mm. in diameter, comparable to those of Sunfire, a cultivar of the present inventors disclosed in pending U.S. application Ser. No. 103,090 filed Dec. 12, 1979 and now abandoned.

4. Leaf size, leaf shape and leaf variegation are also comparable to that of Sunfire.

5. Superior self-branching habit, thus being particularly productive as a cutting producer.

6. Spreading habit and good self-branching make plant highly suitable for growing in hanging baskets.

7. Good keeping qualities if grown outside in Ashtabula, Ohio, where it will flower from planting date in early June until frost kills the plant.

8. Growth rate is slightly smaller than that of Sunfire, producing a dome-shaped plant 25 cm. high and 50 cm. in diameter in 60 days after planting outside, starting from a plant in a 10 cm. pot, as tested in Ashtabula, Ohio, or a saleable 8" to 10" hanging basket, starting from 3 rooted cuttings per basket, in approximately 90 days.

The accompanying colored photograph illustrates the overall appearance of the cultivar, showing the natural flower and foliage colors as true as it is reasonably possible to obtain in a colored reproduction of this type.

The following is a detailed description of the new impatiens cultivar based on plants produced under commercial practices in Ashtabula, Ohio, both in the greenhouses of Mikkelsens Inc., and outdoors in full sunlight. Color references are made to the Royal Horticultural Society Colour Chart except where general terms of ordinary dictionary significance are used.

Parentage:

A controlled cross of Mikkelsen seedling number 76-398-2 as the seed parent and the cultivar Satellite as the pollen parent.

Propagation:

(A) *Type cutting.*—Short tip cutting with stems up to 2 cm. long.

(B) *Time to root.*—10–12 days at 20° C. summer. 14–16 days at 20° C. winter.

(C) *Rooting habit.*—Abundant, fibrous.

Plant description:

(A) *Form.*—Spreading, close internoded, self-branching herb, producing a dome-shaped plant approximately 25 cm. high and 50 cm. in diameter when grown outside, starting from a 10 cm. pot, in approximately 60 days.

(B) *Habit of growth.*—Rate of growth moderate for this type of plant. Vegetative shoots are formed at the lower nodes and flowers at the higher nodes.

(C) *Foliage.*—Leaves simple, lower leaves opposite, upper leaves in whorls of 3 to 6. (1) Size: Average full grown leaf 100 mm. long × 30 mm. wide. Full grown leaves have petioles up to 10 mm. long; young leaves have no petioles. (2) Shape: Elliptic, apex acuminate, base attenuate. (3) Texture: Leathery, glabrous. (4) Margin: Ciliate to very slightly serrulate. (5) Color: Young foliage: top side green 137A; under side green 137C. Mature foliage: top side, outer area green 139A; inner area yellow 10 B-C; under side, outer area green 138A; inner area yellow 10C. (6) Veination: Pinnate.

Flowering description:

(A) *Flowering habits.*—Floriferous, flowers occurring progressively around the whorl of leaves. Flowers are single.

(B) *Natural flowering season.*—Flowering is indeterminate and occurs throughout the year.

(C) *Flower buds.*—Conical, covered with 3 sepals, upper 2 sepals 6 mm. long × 6 mm. wide, apex acuminate to cuspidate, at the base a hollow spur, color red 46A. Spurs of the 2 upper sepals frequently uneven in length, varying from 1 mm. to 30 mm. Lower sepal 12 mm. long × 10 mm. wide, petaloid, asymmetrically funnel form, cuspidate with a spur 50 mm. long if full grown, color red 46A.

(D) *Flowers borne.*—On pedicels, color red 53 B-C, 55 mm. long.

(E) *Quantity of flowers.*—One flower per leaf, occurring progressively around the whorl of leaves.

(F) *Petals.*—(1) Shape: Top petal nearly oblong, lower petals heartshaped. (2) Color: Top side in winter when opening red 46B, fading to red 45C; under side red 43A. (3) Number of petals: Five, the 4 lower petals united in lateral pairs. (4) Size of petals: Top petal 17 mm. long, 23 mm. wide; 2 middle petals 22 mm. long, 22 mm. wide; 2 lower petals 27 mm. long, 27 mm. wide; total flower 50 mm. in diameter.

(G) *Reproductive organs.*—(1) Stamens: Five, lower stamen shorter than the others. (a) anther shape: hooded, color red, with cream apex. (b) pollen color: cream. (c) Stamens united in an asymmetrical tube, covering the ovary. (2) Pistils: (a) stigma shape: Five pointed star, colorless. (b) style shape: Very short, dome-shaped. (c) Ovary: Five celled, size 5 mm. long, color green, infused with red, explosively dehiscent.

Disease resistance:

No general plant diseases observed to date. However, two dotted spider mite can cause plant injury, and thrips can cause injury and stunting of the growing tip.

We claim:

1. A new and distinct cultivar of Impatiens known by the cultivar name Red Planet, as described and illustrated, and particularly characterized by the combined characteristics of good self-branching; spreading habit; highly variegated foliage; striking velvet-like deep-red flowers; early flowering; suitability for growing both outside in full sunlight and in hanging baskets; and by its good keeping quality both outside in full sunlight and in hanging baskets.

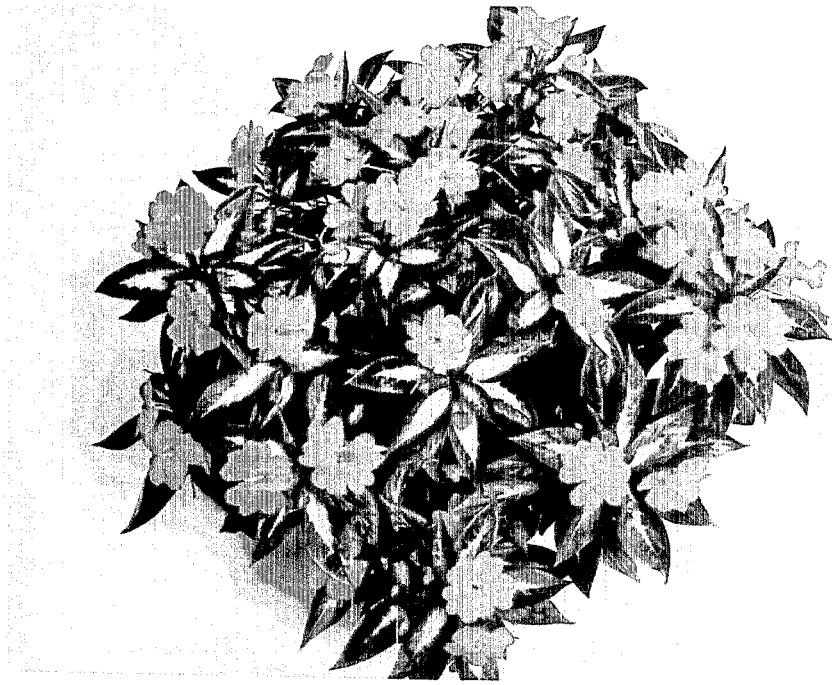

* * * * *